(12) United States Patent
Moschetta et al.

(10) Patent No.: US 10,369,160 B2
(45) Date of Patent: Aug. 6, 2019

(54) METHODS OF TREATING CANCER

(71) Applicant: Intercept Pharmaceuticals, Inc., New York, NY (US)

(72) Inventors: Antonio Moschetta, Bitonto Bari (IT); Jesus Maria Banales Asurmedi, San Sebastián (ES); Luis Bujanda Fernández de Pierola, San Sebastián (ES); María Jesús Perugorria Montiel, San Sebastián (ES); Oihane Erice Azparren, San Sebastián (ES)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/484,379

(22) Filed: Apr. 11, 2017

(65) Prior Publication Data
US 2017/0296556 A1   Oct. 19, 2017

Related U.S. Application Data

(60) Provisional application No. 62/321,816, filed on Apr. 13, 2016, provisional application No. 62/468,259, filed on Mar. 7, 2017.

(51) Int. Cl.
| | | |
|---|---|---|
| *A61K 31/575* | (2006.01) | |
| *A61P 35/00* | (2006.01) | |
| *A61K 31/133* | (2006.01) | |
| *A61K 47/54* | (2017.01) | |
| *A61K 39/00* | (2006.01) | |

(52) U.S. Cl.
CPC .......... *A61K 31/575* (2013.01); *A61K 31/133* (2013.01); *A61K 47/54* (2017.08); *A61K 47/542* (2017.08); *A61P 35/00* (2018.01); *A61K 2039/505* (2013.01)

(58) Field of Classification Search
None
See application file for complete search history.

(56) References Cited

U.S. PATENT DOCUMENTS

| | | |
|---|---|---|
| 7,138,390 B2 | 11/2006 | Pellicciari |
| 7,932,244 B2 | 4/2011 | Pellicciari et al. |
| 8,114,862 B2 | 2/2012 | Pellicciari |
| 9,611,289 B2 | 4/2017 | Pellicciari |
| 2005/0107475 A1 | 5/2005 | Jones et al. |
| 2009/0062526 A1 | 3/2009 | Yu et al. |
| 2014/0148428 A1 | 5/2014 | Pruzanski et al. |
| 2014/0186438 A1 | 7/2014 | Manku et al. |
| 2014/0371190 A1 | 12/2014 | Pellicciari et al. |
| 2015/0359805 A1* | 12/2015 | Pellicciari .................. C07J 9/00 514/182 |

FOREIGN PATENT DOCUMENTS

| | | |
|---|---|---|
| WO | WO 2006/122977 | 11/2006 |
| WO | WO 2013/037482 A1 | 3/2013 |
| WO | WO 2014/066819 | 5/2014 |
| WO | WO 2015/183794 A1 | 12/2015 |

OTHER PUBLICATIONS

Huang et al., "FXR and liver carcinogenesis", Acta Pharmacologica Sinica, vol. 36, pp. 37-43, published online Dec. 15, 2014.*
MedicineNet, "Cancer", http://www.medterms.com, 2004, downloaded Jun. 12, 2010, 2 pages.*
Katzenellengoben, et al. Mol. Cancer Res. 2007, vol. 5, No. 11, p. 1159-1170.
Therasse et al, J. Natl. Cancer Inst., 2000, vol. 92, p. 205-216.
Yang, F. et al. "Spontaneous Development of Liver Tumors in the Absence of the Bile Acid Receptor Farnesoid X Receptor", Cancer Research, 2007, vol. 67, No. 3, p. 863-867.
Dai et al., "Impact of bile acids on the growth of human cholangiocarcinoma via FXR", Journal of Hematology & Oncology, vol. 4, No. 41, p. 1-8 of 8 (2011).
Erice et al., "Differential effects of FXR or TGR5 activation in cholangiocarcinoma progression", BBA—Molecular Basis of Disease, vol. 1864, p. 1335-1344, (2017).
Liu et al. "Ursodeoxycholic acid induces apoptosis in hepatocellular carcinoma xenografts in mice" World Journal of Gastroenterology, 2015, vol. 21, p. 10367-10374.

* cited by examiner

*Primary Examiner* — Savitha M Rao
*Assistant Examiner* — Gregg Polansky
(74) *Attorney, Agent, or Firm* — Michelle Iwamoto-Fan

(57) ABSTRACT

The present invention relates to methods of treating or preventing cancer in a subject in need thereof comprising administering a therapeutically effective amount of a compound of the invention.

6 Claims, 10 Drawing Sheets

MDR2KO

MDR2KO

METHODS OF TREATING CANCER

BACKGROUND TO THE DISCLOSURE

Cancer is characterized primarily by an increase in the number of abnormal cells derived from a given normal tissue, invasion of adjacent tissues by the abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Primary liver cancer is one of the most common forms of cancer in the world. There are two main types of liver cancer: hepatocellular carcinoma (HCC), also known as malignant hepatoma, and cholangiocellular carcinoma. HCC is the most common form of primary liver cancer, and develops within the hepatocyte. HCC occurs mostly in men and patients that suffer from cirrhosis. In contrast, cholangiocellular carcinoma or bile duct cancer develops in the small bile ducts within the liver. This type of cancer is more common among women. HCC is the one of the most common cancers worldwide and the third most common cause of cancer-related deaths. The disease is often diagnosed late in the course of clinical manifestation. As a result, only 10-15% of patients are candidates for curative surgery. For the majority of HCC patients, systemic chemotherapies or supportive therapies are the mainstay treatment options.

Up to the present time, there are a limited number of drugs that can effectively treat cancer such as HCC. For example, patients with metastatic hepatocellular carcinoma or hepatocellular carcinoma, where local treatment has failed, normally survive for only three to four months. Metastatic hepatocellular carcinoma or hepatocellular carcinoma, where local treatment has failed, is mainly subjected to systemic therapy. The use of doxorubicin, a high dosage of tamoxifen in combination doxorubicin or EA-PFL (etoposide, adriamycin, cisplatin, fluorouracil and leucovorin), is an effective example. The remission rate of these drugs can achieve levels between 15 and 30%. However, because the patients of hepatocellular carcinoma usually develop complication of liver cirrhosis and other complications (such as leukopenia, thrombopenia or liver function impairment), they cannot be subject to systemic chemotherapy. Further, most chemotherapeutic agents show limited effectiveness and have not been able to significantly improve patient survival. Despite ongoing efforts, the adverse clinical course of most cancer patients underscores the needs for more efficacious chemotherapies.

The present invention addresses these needs. Therefore, it is the object of the present invention to provide improved methods of treating or preventing cancer such as hepatocellular carcinoma.

SUMMARY OF THE DISCLOSURE

Figure 1A:
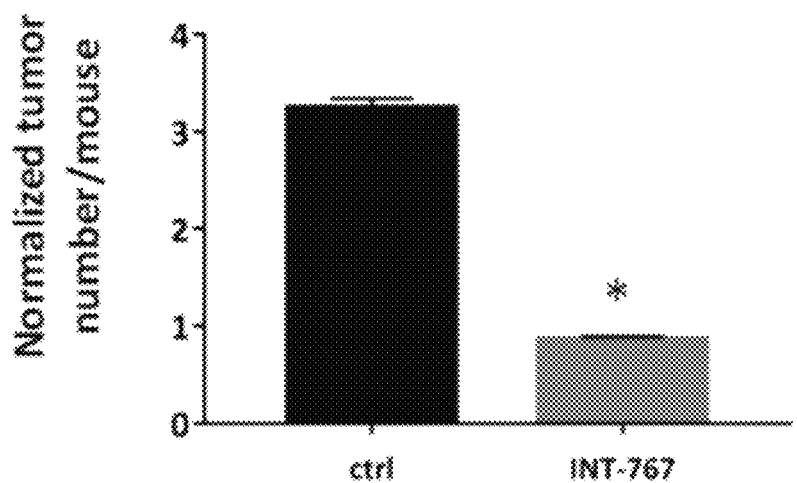
FIG. 1A is a bar graph showing the effects of INT-767 (Compound 1-Na) and control diet on the number of hepatic tumors in multidrug resistance protein 2 (Mdr2$^{-/-}$) knockout mice. *$p<0.01$ vs. control.

The present application relates to methods of treating or preventing cancer in a subject in need thereof comprising administering a therapeutically effective amount of a Farnesoid X Receptor (FXR) agonist. In one embodiment, the FXR agonist is Compound 1 or Compound 2:

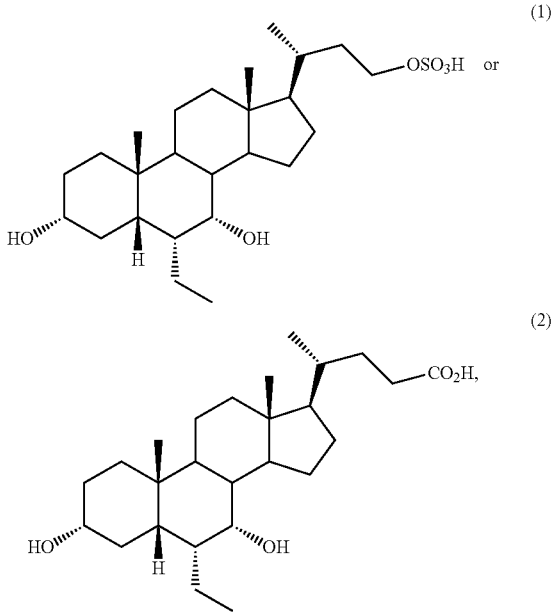

or a pharmaceutically acceptable salt or amino acid conjugate thereof.

In one embodiment, the cancer is selected from the group consisting of hepatocellular carcinoma, pancreatic cancer, kidney cancer, prostate cancer, esophageal cancer, breast cancer, gastric cancer, renal cancer, salivary gland cancer, ovarian cancer, uterine body cancer, bladder cancer, and lung cancer. In one embodiment, the cancer is hepatocellular carcinoma. In one embodiment, the cancer is pancreatic cancer. In one embodiment, the cancer is kidney cancer. In one embodiment, the cancer is prostate cancer. In one embodiment, the cancer is esophageal cancer. In one embodiment, the cancer is breast cancer. In one embodiment, the cancer is gastric cancer. In one embodiment, the cancer is renal cancer. In one embodiment, the cancer is salivary gland cancer. In one embodiment, the cancer is ovarian cancer. In one embodiment, the cancer is uterine body cancer. In one embodiment, the cancer is lung cancer.

In one embodiment, the FXR agonist is Compound 1 or a pharmaceutically acceptable salt thereof. In another embodiment, the FXR agonist is the sodium salt of Compound 1 (i.e., Compound 1-Na). In yet another embodiment, the FXR agonist is the N,N-diethylethaneamine salt of Compound 1 (i.e. Compound 1-DEA).

In another embodiment, the FXR agonist is Compound 2 or a pharmaceutically acceptable salt or amino acid conjugate thereof. In one embodiment, the FXR agonist is the glycine conjugate of Compound 2. In one embodiment, the FXR agonist is the taurine conjugate of Compound 2. In one embodiment, the FXR agonist is the sarcosine conjugate of Compound 2.

The present invention further relates to the use of Compound 1 or a pharmaceutically acceptable salt thereof or Compound 2 or a pharmaceutically acceptable salt or amino acid conjugate thereof in the manufacture of a medicament for treating or preventing cancer in a subject in need thereof.

The present invention further relates to Compound 1 or a pharmaceutically acceptable salt thereof and Compound 2 or a pharmaceutically acceptable salt or amino acid conjugate thereof for use in treating or preventing cancer in a subject in need thereof.

The present invention also relates a pharmaceutical composition comprising Compound 1 or a pharmaceutically acceptable salt thereof and Compound 2 or a pharmaceutically acceptable salt or amino acid conjugate thereof for treating or preventing cancer in a subject in need thereof and a pharmaceutically acceptable excipient.

The present invention further relates to a kit for treating or preventing cancer in a subject in need thereof comprising Compound 1 or a pharmaceutically acceptable salt thereof and Compound 2 or a pharmaceutically acceptable salt or amino acid conjugate thereof.

DETAILED DESCRIPTION OF THE DISCLOSURE

The present invention is based at least in part on the discovery that Compounds 1 and 2 were effective in treating cancer in animal models predictive of cancer. As described in the examples below, the inventors have discovered that a compound of the invention suppressed tumor growth in murine models of spontaneous hepatocarcinogenesis.

Definitions

For convenience, certain terms used in the specification, examples and appended claims are collected here.

The term "cancer" as used herein refers to any of the diseases characterized by the presence of cancerous tissue in a subject.

As used herein, "cancerous tissue" refers to a tissue that comprises malignant neoplastic cells, exhibits an abnormal growth of cells and/or hyperproliferative cells. Cancerous tissue can be a primary malignant tumor, arising from a tissue or organ of origin, or it can be a metastatic malignant tumor, growing in a body tissue which was not the source of the original tumor.

As used herein, the term "tumor" can include a solid tumor or a cancer of hematopoietic origin. In some embodiments the tumor may be characterized by its ability to invade surrounding tissues, to metastasize to other parts of the body, and/or by its angiogenic activity. Exemplary tumors result from hepatocellular carcinoma, gastric cancer, renal cancer, prostate cancer, adrenal cancer, pancreatic cancer, breast cancer, bladder cancer, salivary gland cancer, ovarian cancer, uterine body cancer, and lung cancer.

As used herein, the term "invasive" refers to the process by which a cell, a group of cells, or a malignancy spreads from a site to adjacent sites.

The term "metastatic", as used herein, refers to the process by which a cell, a group of cells, or a malignancy spreads from a site to sites not adjacent to the first site.

As used herein, "hepatocellular carcinoma", "HCC", and "malignant hepatoma" are used interchangeably and refer to primary and secondary (metastasized) tumors that originate from the liver tissue. The term "refractory hepatocellular carcinoma" as used herein refers to hepatocellular carcinoma that fails to respond favorably to an antineoplastic treatment. Accordingly, "a hepatocellular carcinoma refractory to a treatment" as used herein refers to a hepatocellular carcinoma that fails to respond favorably to, or resistant to the treatment, or alternatively, recurs or relapses after responding favorably to the treatment.

As used herein, the term "Compound 1" refers to

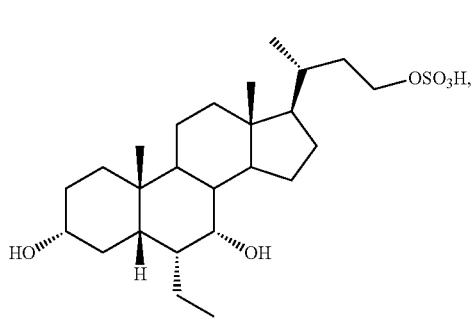

(1)

which is also known as 6α-ethyl-3α7α,23-trihydroxy-24-nor-5β-cholan-23-hydrogen sulphate. "Compound 1-Na" or "1-Na" which is also known as INT-767 or 6α-ethyl-3α,7α,23-trihydroxy-24-nor-5β-cholan-23-sulphate sodium" are used interchangeably and refer to the sodium salt of Compound 1. As used herein, "Compound 1-DEA" or "1-DEA" which is also known as 6α-ethyl-3α,7α,23-trihydroxy-24-nor-5β-cholan-23-sulphate N,N-diethylethaneamine" are used interchangeably and refer to the N,N-diethylethaneamine salt of Compound 1. The structures of Compound 1-Na and Compound 1-DEA are provided below.

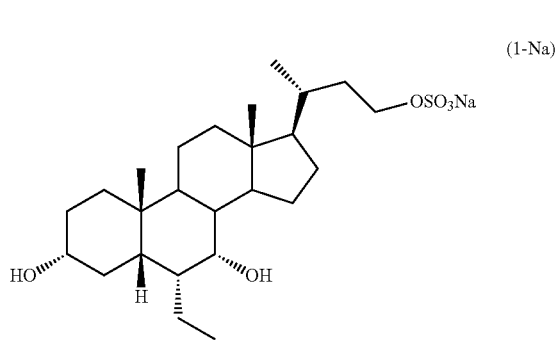

(1-Na)

(1-DEA)

"Compound 2" as used herein refers to

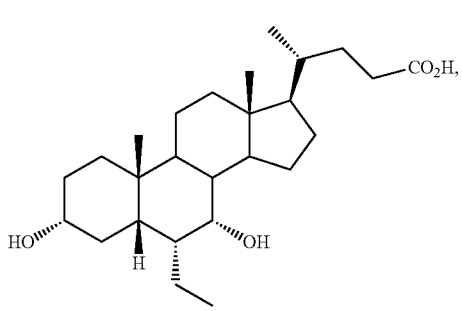

(2)

which is also known as obeticholic acid, INT-747, 6-ECDCA, 6-alpha-ethyl chenodeoxycholic acid, or 6α-ethyl-3α,7α-dihydroxy-5β-cholan-24-oic acid.

As used herein, "Compound 3" refers to

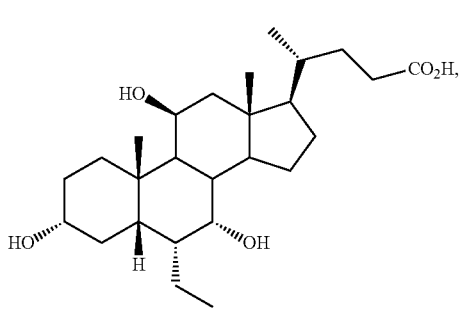

(3)

which is also known as 3α,7α,11β-trihydroxy-6α-ethyl-5β-cholan-24-oic acid.

The phrase a "compound of the invention" as used herein encompasses Compounds 1, 1-Na, 1-DEA, 2, and 3, or a pharmaceutically acceptable salt or amino acid conjugate thereof.

The term "treating" as used herein refers to any indicia of success in the treatment or amelioration of the cancer. Treating can include, for example, reducing or alleviating the severity of one or more symptoms of the cancer, or it can include reducing the frequency with which symptoms of a disease, defect, disorder, or adverse condition, and the like, are experienced by a patient. "Treating" can also refer to reducing or eliminating a condition of a part of the body, such as a cell, tissue or bodily fluid, e.g., blood.

As used herein, the term "preventing" refers to the partial or complete prevention of the cancer in an individual or in a population, or in a part of the body, such as a cell, tissue or bodily fluid (e.g., blood). The term "prevention" does not establish a requirement for complete prevention of a disease or condition in the entirety of the treated population of individuals or cells, tissues or fluids of individuals. The term "treat or prevent" is used herein to refer to a method that results in some level of treatment or amelioration of the cancer, and contemplates a range of results directed to that end, including but not restricted to prevention of the cancer entirely.

The phrase "therapeutically effective amount" as used herein refers to an effective amount comprising an amount sufficient to cause a tumor to shrink and/or to decrease the growth rate of the tumor (such as to suppress tumor growth)

or to prevent or delay other unwanted cell proliferation in cancer. In some embodiments, an effective amount is an amount sufficient to delay the development of cancer. In some embodiments, an effective amount is an amount sufficient to prevent or delay recurrence. An effective amount can be administered in one or more administrations. In the case of HCC or CRC, the effective amount of the drug or composition may: (i) reduce the number of tumor cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor, and/or (vii) relieve to some extent one or more of the symptoms associated with cancer.

The term "regimen" as used herein refers to a protocol for dosing and/or timing the administration a compound of the invention for treating cancer. A regimen can include periods of active administration and periods of rest as known in the art. Active administration periods include administration of a compound of the invention in a defined course of time, including, for example, the number of and timing of dosages of the compositions. In some regimens, one or more rest periods can be included where no compound is actively administered, and in certain instances, includes time periods where the efficacy of such compounds can be minimal.

As used herein, "combination therapy" refers to a compound of the invention can be administered in conjunction with another therapeutic agent. "In conjunction with" refers to administration of one treatment modality in addition to another treatment modality, such as administration of a compound of the invention as described herein in addition to administration of another therapeutic agent to the same subject. As such. "in conjunction with" refers to administration of one treatment modality before, during, or after delivery of a second treatment modality to the subject.

As used herein, "pharmaceutically acceptable" refers to a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have met the required standards of toxicological and manufacturing testing and/or are included on the Inactive Ingredient Guide prepared by the U.S. Food and Drug administration.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to practice the disclosed methods or to make and used the disclosed compounds and in the claimed methods.

Methods of Treating Cancer

The present invention is based at least in part based on the discovery that a compound of the invention is effective in treating cancer in murine models predictive of cancer in humans. Accordingly, the present application relates to methods of treating or preventing cancer in a subject in need thereof comprising administering therapeutically effective amount of a FXR agonist selected from the group consisting of Compounds 1, 1-Na. 1-DEA, 2, and 3:

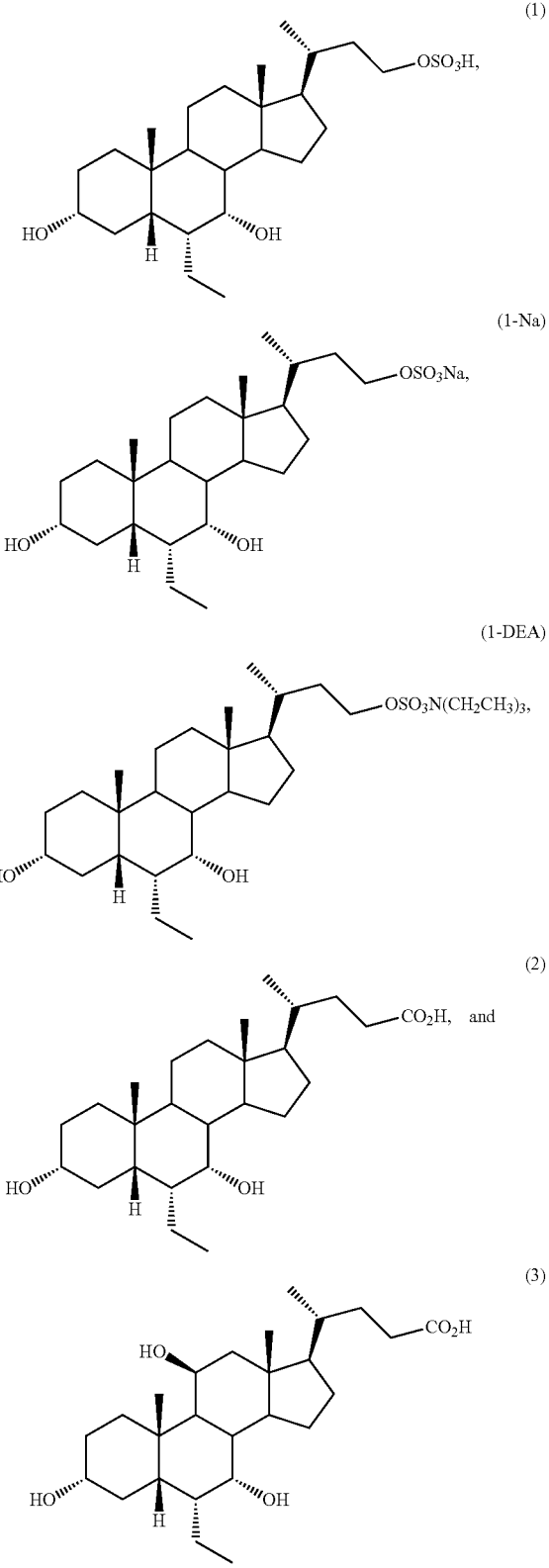

or a pharmaceutically acceptable salt or amino acid conjugate thereof. In one embodiment, the FXR agonist is Compound 1. In one embodiment, the FXR agonist is Compound 1-Na. In another embodiment, the FXR agonist is Compound 1-DEA. In one embodiment, the FXR agonist is Compound 2. In one embodiment, the FXR agonist is Compound 3.

In the methods described herein, exemplary cancers are selected from the group consisting of hepatocellular carcinoma, pancreatic cancer, prostate cancer, esophageal cancer, breast cancer, gastric cancer, renal cancer, salivary gland cancer, ovarian cancer, uterine body cancer, bladder cancer, and lung cancer. The appropriate treatment regimen for cancer depends on the type of cell from which the tumor derived, the stage and severity of the malignancy, and the genetic abnormality that contributes to the tumor.

Cancer staging systems describe the extent of cancer progression. In general, the staging systems describe how far the cancer has spread and puts patients with similar prognosis and treatment in the same staging group. In general, there are poorer prognoses for tumors that have become invasive or metastasized. In one type of staging system, cases are grouped into four stages, denoted by Roman numerals I to IV. In stage I, cancers are often localized and are usually curable. Stage II and IIIA cancers are usually more advanced and may have invaded the surrounding tissues and spread to lymph nodes. Stage IV cancers include metastatic cancers that have spread to sites outside of lymph nodes.

Another staging system is TNM staging which stands for the categories: Tumor, Nodes, and Metastases. In this system, malignancies are described according to the severity of the individual categories. For example, T classifies the extent of a primary tumor from 0 to 4 with 0 representing a malignancy that does not have invasive activity and 4 representing a malignancy that has invaded other organs by extension from the original site. N classifies the extent of lymph node involvement with 0 representing a malignancy with no lymph node involvement and 4 representing a malignancy with extensive lymph node involvement. M classifies the extent of metastasis from 0 to 1 with 0 representing a malignancy with no metastases and 1 representing a malignancy with metastases.

These staging systems or variations of these staging systems or other suitable staging systems may be used to describe a tumor. Few options are available for the treatment of cancer depending on the stage and features of the cancer. Treatments include surgery, treatment with sorafenib, and targeted therapies. In general, surgery is the first line of treatment for early stage localized cancer. Additional systemic treatments may be used to treat invasive and metastatic tumors.

In accordance with one aspect of the present invention, a method is provided for treating hepatocellular carcinoma (or malignant hepatoma). Specifically, the method comprises treating a subject in need thereof having hepatocellular carcinoma with a therapeutically effective amount of a compound of the invention. That is, the present invention is directed to the use a compound of the invention for the manufacture of medicaments for treating hepatocellular carcinoma patients identified or diagnosed as having hepatocellular carcinoma. In separate embodiments, the treatment method optionally comprises a step of diagnosing or identifying a patient as having hepatocellular carcinoma. The identified patient is then treated with or administered with a therapeutically effective amount of a compound of the invention. Hepatocellular carcinoma can be diagnosed in any conventional diagnostic methods known in the art including ultrasound, CT scan, MRI, alpha-fetoprotein testing, des-gamma carboxyprothrombin screening, and biopsy.

The present invention also provides a method of treating refractory hepatocellular carcinoma comprising treating a patient identified as having refractory hepatocellular carcinoma with a therapeutically effective amount of a compound of the invention. In specific embodiments, the patient has a hepatocellular carcinoma that is refractory to a treatment comprising one or more drugs selected from the group consisting of sorafenib, regorafenib, anthracyclines (e.g., doxorubicin, daunorubicin, epirubicin, idarubicin), platinum agents (e.g., cisplatin, carboplatin, oxaliplatin, picoplatin), 5-FU and capecitabine. The present invention is also directed to the use of a compound of the invention for the manufacture of medicaments for treating refractory hepatocellular carcinoma, e.g., a hepatocellular carcinoma refractory to one or more drugs selected from sorafenib, regorafenib, anthracyclines (e.g., doxorubicin, daunorubicin, epirubicin, idarubicin), platinum agents (cisplatin, carboplatin, oxaliplatin, picoplatin), 5-FU and capecitabine.

To detect a refractory hepatocellular carcinoma, patients undergoing initial treatment can be carefully monitored for signs of resistance, non-responsiveness or recurring hepatocellular carcinoma. This can be accomplished by monitoring the patient's cancer's response to the initial treatment which, e.g., may include one or more drugs selected from the group consisting of sorafenib, regorafenib, doxorubicin, daunorubicin, epirubicin, idarubicin, cisplatin, carboplatin, oxaliplatin, picoplatin, 5-FU, tegafur and capecitabine. The response, lack of response or relapse of the cancer to the initial treatment can be determined by any suitable method practiced in the art. For example, this can be accomplished by the assessment of tumor size and number. An increase in tumor size or, alternatively, tumor number, indicates that the tumor is not responding to the chemotherapy or that a relapse has occurred. The determination can be done according to the "RECIST" criteria as described in detail in Therasse et al, J. Natl. Cancer Inst. 92:205-216 (2000).

In accordance with yet another aspect of the present invention, a method is provided for preventing or delaying the onset of hepatocellular carcinoma (or hepatocellular carcinoma), or preventing or delaying the recurrence of hepatocellular carcinoma, which comprises treating a patient in need of the prevention or delay with a prophylactically effective amount of a compound of the invention.

It is known that subjects with hepatitis B or hepatitis C infection, or having cirrhosis have an increased risk of developing hepatocellular carcinoma. In addition. people who have acute and chronic hepatic porphyrias (acute intermittent porphyria, porphyria cutanea tarda, hereditary coproporphyria, variegate porphyria ) and tyrosinemia type I are also at an increased risk of for developing hepatocellular carcinoma. These people can all be candidates for the method of the present invention for preventing or delaying the onset of hepatocellular carcinoma using a prophylactically effective amount of a compound of the invention. In addition, patients with a family history of hepatocellular carcinoma can also be identified for the application of the present method of preventing or delaying the onset of hepatocellular carcinoma. For purposes of preventing or delaying the recurrence of hepatocellular carcinoma, hepatocellular carcinoma patients who have been treated and are in remission or in a stable or progression free-state may be treated with a prophylactically effective amount of a compound of the invention to effectively prevent or delay the recurrence or relapse of hepatocellular carcinoma.

One embodiment is a method of treating pancreatic cancer by administering a therapeutically effective amount of a compound of the invention. Another embodiment is a method of treating prostate cancer by administering a therapeutically effective amount of a compound of the invention. Another embodiment is a method of treating kidney cancer by administering a therapeutically effective amount of a compound of the invention. Another embodiment is a method of treating prostate cancer by administering a therapeutically effective amount of a compound of the invention. In still another embodiment is a method of treating esophageal cancer by administering a therapeutically effective amount of a compound of the invention. In still another embodiment is a method of treating breast cancer by administering a therapeutically effective amount of a compound of the invention. One embodiment is a method of treating gastric cancer by administering a therapeutically effective amount of a compound of the invention. In another embodiment is a method of treating renal cancer by administering a therapeutically effective amount of a compound of the invention. In still another embodiment is a method of treating salivary gland cancer by administering a therapeutically effective amount of a compound of the invention. In still another embodiment is a method of treating ovarian cancer by administering a therapeutically effective amount of a compound of the invention. One embodiment is a method of treating uterine body cancer by administering a therapeutically effective amount of a compound of the invention. In another embodiment is a method of treating bladder cancer by administering a therapeutically effective amount of a compound of the invention. In still another embodiment is a method of treating lung cancer by administering a therapeutically effective amount of a compound of the invention.

In instances where a compound of the invention is useful for the treatment of a cancer described herein, such compounds can be co-administered with a second agent. The second agent useful in methods of treating cancers provided herein can include any known class of anti-cancer agents such as, for example, radiation therapy, operations, alkylating agents, antimetabolites, anthracyclines, campothecins, vinca alkaloids, taxanes or platinums, as well as other antincoplastic agents known in the art. Such anti-cancer agent and antineoplastic agent classifications are known in the art and used in accordance with their plain and ordinary meaning.

Exemplary anti-cancer agents include but are not limited to: ABRAXANE; abiraterone; ace-11; aclarubicin; acivicin; acodazole hydrochloride; acronine; actinomycin; acylfulvene; adecypenol; adozelesin; adriamycin; aldesleukin; all trans-retinoic acid (ATRA); altretamine; ambamustine; ambomycin; ametantrone acetate; amidox; amifostine; aminoglutethimide; aminolevulinic acid; amrubicin; amsacrine; anagrelide; anastrozole; andrographolide; antarelix; anthramycin; aphidicolin glycinate; apurinic acid; ara-CDP-DL-PTBA; arginine deaminase; ARRY-162; ARRY-300; ARRY-142266; AS703026; asparaginase; asperlin; asulacrine; atamestane; atrimustine; AVASTIN: axinastatin 1; axinastatin 2; axinastatin 3; azasetron; azatoxin; azatyrosine; azacitidine; AZD8330; azetepa; azotomycin; balanol; batimastat; BAY 11-7082; BAY 43-9006; BAY 869766; bendamustine; benzochlorins; benzodepa; benzoylstaurosporine; beta-alethine; betaclamycin B; betulinic acid; b-FGF inhibitor; bicalutamide; bisantrene; bisaziridinylspermine; bisnafide; bisnafide dimesylate; bistratene A; bisantrene hydrochloride; bleomycin; bleomycin sulfate; busulfan; bizelesin; breflate; bortezomib; brequinar sodium; bropirimine; budotitane; buthionine sulfoximine; bryostatin; cactinomycin; calusterone; calcipotriol; calphostin C; camptothecin derivatives; capecitabine; carboxamide-amino-triazole; carboxyamidotriazole; CaRest M3; CARN 700; caracemide; carbetimer; carboplatin; carmustine; carubicin hydrochloride; carzelesin; castanospermine; cecropin B; cedefingol; celecoxib; cetrorelix; chlorins; chloroquinoxaline sulfonamide; cicaprost; chlorambucil; Chlorofusin; cirolemycin; cisplatin; CI-1040; cis-porphyrin; cladribine; clomifene analogues; clotrimazole; collismycin A; collismycin B; combretastatin A4; combretastatin analogue; conagenin; crambescidin 816; crisnatol; crisnatol mesylate; cryptophycin 8; cryptophycin A derivatives; curacin A; cyclopentanthraquinones; cycloplatam; cypemycin: cyclophosphamide; cytarabine; cytarabine ocfosfate; cytolytic factor; cytostatin; dacarbazine; dactinomycin; daunorubicin; daunorubicin hydrochloride; decarbazine; dacliximab; dasatinib; decitabine; dehydrodidemnin B; deslorelin; dexamethasone; dexifosfamide; dexrazoxane; dexverapamil; dexormaplatin; dezaguanine; dezaguanine mesylate; diaziquone; didemnin B; didox; diethylnorspermine; dihydro 5 azacytidine; dihydrotaxol; 9-dioxamycin; diphenyl spiromustine; docosanol; dolasetron; docetaxel; doxorubicin; doxorubicin hydrochloride; doxifluridine; droloxifene; droloxifene citrate: dromostanolone propionate; dronabinol; duazomycin; duocarmycin SA; ebselen; ecomustine, edelfosine; edrecolomab; edatrexate; eflornithine hydrochloride; eflomithine; elemene; emitefur; elsamitrucin; enloplatin; enpromate; epipropidine; epirubicin; epirubicin hydrochloride; epristeride; erbulozole; eribulin; esorubicin hydrochloride; estramustine; estramustine phosphate sodium; etanidazole; etoposide; etoposide phosphate; etoprine; exemestane; fadrozole; fadrozole hydrochloride; fazarabine; fenretinide; filgrastim; finasteride; flavopiridol; flezelastine; fluasterone; floxuridine; fludarabine phosphate; fludarabine; fluorodaunorubicin hydrochloride; forfenimex; formestane; fluorouracil; floxouridine; flurocitabine; fosquidone; fostriecin sodium; fostriecin; fotemustine; gadolinium texaphyrin; gallium nitrate; galocitabine; ganirelix; gelatinase inhibitors; gemcitabine; geldanamycin; gossyphol; GDC-0973; GSK 1120212/tramctinib; herceptin; hydroxyurea; hepsulfam; hereregulin; hexamethylene bisacetamide; hypericin; ibandronic acid; ibrutinib, idarubicin; idarubicin hydrochloride; ifosfamide; canfosfamide; ilmofosine; iproplatin; idoxifene; idramantone; ilmofosine; ilomastat; imidazoacridones; imatinib (e.g., GLEEVEC); imiquimod; iniparib (BSI 201); iobenguane; iododoxorubicin; ipomeanol; irinotecan; irinotecan hydrochloride; irsogladine; isobengazole; isohomohalicondrin B; itasetron; iimofosine; interleukin IL-2 (including recombinant interleukin II; or rIL.sub.2); interferon alfa-2a; interferon alfa-2b; interferon alfa-n1; interferon alfa-n3; interferon beta-1a; interferon gamma-1b; jasplakinolide; kahalalide F; lamellarin N triacetate; lanreotide; leinamycin; lenograstim; lentinan sulfate; leptolstatin; letrozole; leuprorelin; levamisole; lenalidomide; lenvatinib; liarozole; lissoclinamide 7; lobaplatin; lombricine; lometrexol; lonidamine; losoxantrone; lovastatin; loxoribine; lurtotecan; lutetium texaphyrin; lysofylline; lanreotide acetate; lapatinib; letrozole; leucovorin; leuprolide acetate; liarozole hydrochloride; lometrexol sodium; lomustine; losoxantrone hydrochloride; pomalidomide; LY294002; maitansine; mannostatin A; marimastat; masoprocol; maspin; matrilysin inhibitors; menogaril; merbarone; meterelin; methioninase; metoclopramide; MIF inhibitor; mifepristone; miltefosine; mirimostim; mitoguazone; mitolactol; mitonafide; mitoxantrone; mofarotene; molgramostim; mopidamol; mycaperoxide B; myriaporone; maytansine; mechlorethamine hydrochloride; megestrol acetate; melengestrol acetate; melphalan; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nafarelin; nagrestip; napavin; naphterpin; nartograstim; nedaplatin; nemorubicin; neridronic acid; nilutamide; nisamycin; nitric oxide modulators; nitroxide antioxidant; nitrullyn; nocodazole; nogalamycin; oblimersen (GENASENSE); octreotide; okicenone; olaparib (LYNPARZA); oligonucleotides; onapristone: ondansetron; oracin; oral cytokine inducer; ormaplatin; oxisuran; oxaloplatin; osaterone; oxaliplatin; oxaunomycin; palauamine; palmitoylrhizoxin; pamidronic acid; panaxytriol; panomifene; parabactin; PARP (polyADP ribose polymerase) inhibitors; pazelliptine; pegaspargase; peldesine; pentosan polysulfate sodium, pentostatin; pentrozole; perflubron: perfosfamide; perillyl alcohol; phenazinomycin; phenylacetate; phosphatase inhibitors; picibanil; pilocarpine hydrochloride; pirarubicin; piritrexim; placetin A; placetin B: porfiromycin; prednisone; prostaglandin J2; pyrazoloacridine; paclitaxel; PD035901: PD 184352; PD318026; PD98059; peliomycin; pentamustine; peplomycin sulfate: PKC412; pipobroman; piposulfan; piroxantrone hydrochloride; plicamycin; plomestane; podophyllotoxin; polyphenol E; porfimer sodium; porfiromycin; prednimustine: procarbazine; procarbazine hydrochloride; puromycin; puromycin hydrochloride; pyrazofurin; raltitrexed; ramosetron; retelliptine demethylated; rhizoxin; rituximab; RII retinamide; rogletimide; rohitukine; romurtide; roquinimex; rubiginone B1; ruboxyl; riboprine; romidepsin; rucaparib; safingol; safingol hydrochloride; saintopin; sarcophytol A; sargramostim; semustine; sizofiran; sobuzoxane; sodium borocaptate; sodium phenylacetate; solverol; sonermin; sorafenib; sunitinib; sparfosic acid; spicamycin D; spiromustine; splenopentin; spongistatin 1; Spongistatin 2; Spongistatin 3; Spongistatin 4; Spongistatin 5; Spongistatin 6; Spongistatin 7; Spongistatin 8; and Spongistatin 9; squalamine; stipiamide; stromelysin inhibitors; sulfinosine; suradista; suramin: swainsonine; SB239063; selumetinib/AZD6244; simtrazene; SP600125; sparfosate sodium; sparsomycin; spirogermanium hydrochloride; spiroplatin; streptonigrin: streptozocin; sulofenur; tallimustine; tamoxifen methiodide; talazoparib (BMN 673); tauromustine; tazarotene; tecogalan sodium; tegafur; tellurapyrylium; temoporfin; temozolomide; teniposide; tetrachlorodccaoxide; tetrazomine; thaliblastine; thiocoraline; thrombopoietin; thymalfasin; thymopoietin receptor agonist; thymotrinan; tirapazamine; titanocene bichloride; topsentin; toremifene; tretinoin; triacetvluridine; triciribine: trimetrexate; triptorelin; tropisetron; turosteride; tyrphostins; talisomycin; TAK-733; taxotere; tegafur; teloxantrone hydrochloride; teroxirone; testolactone; thiamiprine: thioguanine; thiotepa; tiazofurin; tirapazamine; toremifene citrate; trastuzumab; trestolone acetate; triciribine phosphate; trimetrexate; trimetrexate glucuronate; triptorelin; tubulozole hydrochloride; tumor necrosis factor-related apoptosis-inducing ligand (TRAIL); UBC inhibitors; ubenimex; U0126; uracil mustard; uredepa; vapreotide; variolin B; velaresol; veliparib (ABT-888); veramine; verteporfin; vinorelbine; vinxaltine; vitaxin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; wortmannin; XL518; zanoterone; zeniplatin; zilascorb: zinostatin stimalamer; zinostatin; and zorubicin hydrochloride.

Other exemplary anti-cancer agents include Erbulozole (e.g., R-55104); Dolastatin 10 (e.g., DLS-10 and NSC-376128); Mivobulin isethionate (e.g., CI-980); NSC-639829; Discodermolide (e.g., NVP-XX-A-296); ABT-751 (Abbott; e.g., E-7010); Altorhyrtin A; Altorhyrtin C; Cemadotin hydrochloride (e.g., LU-103793 and NSC-D-669356); CEP 9722; Epothilone A; Epothilone B; Epothilone C; Epothilone D; Epothilone E; Epothilone F; Epothilone B N-oxide; Epothilone A N-oxide; 16-aza-epothilone B; 21-aminoepothilone B; 21-hydroxyepothilone D; 26-fluoroepothilone; Auristatin PE (e.g., NSC-654663); Soblidotin (e.g., TZT-1027); LS-4559-P (Pharmacia; e.g., LS-4577); LS-4578 (Pharmacia; e.g., LS-477-P); LS-4477 (Pharmacia); LS-4559 (Pharmacia); RPR-112378 (Aventis); DZ-3358 (Daiichi); FR-182877 (Fujisawa; e.g., WS-9265B); GS-164 (Takeda); GS-198 (Takeda); KAR-2 (Hungarian Academy of Sciences); BSF-223651 (BASF; e.g., ILX-651 and LU-223651); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (e.g., LY-355703); AC-7739 (Ajinomoto; e.g., AVE-8063A and CS-39.HCl); AC-7700 (Ajinomoto; e.g., AVE-8062; AVE-8062A; CS-39-L-Ser.HCl; and RPR-258062A); Vitilevuamide; Tubulysin A; Canadensol; CA-170 (Curis, Inc.); Centaureidin (e.g., NSC-106969); T-138067 (Tularik; e.g., T-67; TL-138067 and TI-138067); COBRA-1 (Parker Hughes Institute; e.g., DDE-261 and WHI-261); H10 (Kansas State University); H16 (Kansas State University); Oncocidin AI (e.g., BTO-956 and DIME); DDE-313 (Parker Hughes Institute); Fijianolide B; Laulimalide; SPA-2 (Parker Hughes Institute); SPA-1 (Parker Hughes Institute; e.g., SPIKET-P); 3-IAABU (Cytoskeleton/Mt. Sinai School of Medicine; e.g., MF-569); Narcosine (e.g., NSC-5366); Nascapine; D-24851 (Asta Medica); A-105972 (Abbott); Hemiasterlin; 3-BAABU (Cytoskeleton/Mt. Sinai School of Medicine; e.g., MF-191); TMPN (Arizona State University); Vanadocene acetylacetonate; T-138026 (Tularik); Monsatrol; Inanocine (e.g., NSC-698666); 3-IAABE (Cytoskeleton/Mt. Sinai School of Medicine); A-204197 (Abbott); T-607 (Tularik; e.g., T-900607); RPR-115781 (Aventis); Eleutherobins (e.g., Desmethyleleutherobin; Desaetyleleutherobin; Isoeleutherobin A; and Z-Eleutherobin); Caribaeoside; Caribaeolin; Halichondrin B; D-64131 (Asta Medica); D-68144 (Asta Medica); Diazonamide A; A-293620 (Abbott); NPI-2350 (Nereus); Taccalonolide A; TUB-245 (Aventis); A-259754 (Abbott); Diozostatin; (−)-Phenylahistin (e.g., NSCL-96F037); D-62638 (Asta Medica); D-62636 (Asta Medica); Myoseverin B; D-43411 (Zentaris; e.g., D-81862); A-289099 (Abbott); A-318315 (Abbott); HTI-286 (e.g., SPA-110; trifluoroacetate salt) (Wyeth); D-82317 (Zentaris); D-82318 (Zentaris); SC-12983 (NCI); Resverastatin phosphate sodium; BPR-OY-007 (National Health Research Institutes); and SSR-250411 (Sanofi)); goserelin; leuprolide; triptolide; homoharringtonine; topotecan; itraconazole; deoxyadenosine; sertraline; pitavastatin; clofazimine; 5-nonyloxytryptamine; vemurafenib; dabrafenib; gefitinib (IRESSA); erlotinib (TARCEVA); cetuximab (ERBITUX); lapatinib (TYKERB); panitumumab (VECTIBIX); vandetanib (CAPRELSA); afatinib/BIBW2992; CI-1033/canertinib; neratinib/HKI-272; CP-724714; TAK-285; AST-1306; ARRY334543; ARRY-380; AG-1478; dacomitinib/PF299804; OSI-420/desmethyl erlotinib; AZD8931; AEE726; pelitinib/EKB-569; CUDC-101; WZ8040; WZ4002; WZ3146; AG-490; XL647; PD 153035; 5-azathioprine; 5-aza-2'-deoxycytidine; 17-N-Allylamino-17-Demethoxygeldanamycin (17-AAG); 20-epi-1,25 dihydroxyvitamin D3; 5 ethynyluracil; and BMS-599626.

One embodiment is a method for treating patients with hepatocellular carcinoma (optionally refractory) by administering a compound of the invention in combination with capecitabine and/or PLX4032 (Plexxikon).

In another embodiment is a method for treating hepatocellular carcinoma (optionally refractory) by administering a compound of the invention in combination with capecitabine, xeloda, and/or CPT-11.

In another embodiment is a method for treating hepatocellular carcinoma (optionally refractory) by administering a compound of the invention in combination with capecitabine, xeloda, and/or CPT-11.

In another embodiment is a method for treating patients with hepatocellular carcinoma (optionally refractory) or patients with unresectable or metastatic hepatocellular carcinoma by administering a compound of the invention in combination with capecitabine and irinotecan.

In another embodiment is a method for treating patients with unresectable or metastatic hepatocellular carcinoma by administering a compound of the invention in combination with interferon alpha or capecitabin.

In another embodiment is a method for treating patients with pancreatic cancer by administering a compound of the invention in combination with gemcitabine.

Pharmaceutical Compositions

A "pharmaceutical composition" is a formulation containing a compound of the invention in a form suitable for administration to a subject. In one embodiment, the pharmaceutical composition is in bulk or in unit dosage form. It can be advantageous to formulate compositions in dosage unit form for ease of administration and uniformity of dosage. The specification for the dosage unit forms are dictated by and directly dependent on the unique characteristics of the active reagent and the particular therapeutic effect to be achieved.

Possible formulations include those suitable for oral, sublingual, buccal, parenteral (e.g., subcutaneous, intramuscular, or intravenous), rectal, topical including transdermal, intranasal and inhalation administration. Most suitable means of administration for a particular patient will depend on the nature and severity of the disease being treated or the nature of the therapy being used and on the nature of the active compound, but where possible, oral administration may be used for the prevention and treatment cancer. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising a compound of the invention and typically a flavored base, such as sugar and acacia or tragacanth and pastilles comprising the active compound in an inert base, such as gelatin and glycerin or sucrose acacia.

Formulations suitable for parenteral administration typically comprise sterile aqueous solutions containing a predetermined concentration of the active compound; the solution may be isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions may be administered intravenously, they may also be administered by subcutaneous or intramuscular injection.

Formulations suitable for rectal administration may be provided as unit-dose suppositories comprising a compound of the invention in one or more solid carriers forming the suppository base. for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing a compound of the invention with liquids or finely divided solid carriers or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent. Suitable formulations for administration by inhalation include fine particle dusts or mists which may be generated by means of various types of metered dose pressurized aerosols, nebulizers, or insufflators.

For pulmonary administration via the mouth, the particle size of the powder or droplets is typically in the range about 0.5-10 μm or 1-5 μm, to ensure delivery into the bronchial tree. For nasal administration, a particle size in the range about 10-500 μm may be used to ensure retention in the nasal cavity.

Metered dose inhalers are pressurized aerosol dispensers, typically containing a suspension or solution formulation of a compound of the invention in a liquefied propellant. During use, these devices discharge the formulation through a valve adapted to deliver a metered volume, typically from about 10 to 150 μm, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents.

Nebulizers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulizers consist of the active ingredient in a liquid carrier and comprise up to about 40% w/w of the formulation, and may comprise less than about 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent. such as lactose, and an optional surfactant. The active ingredient typically comprises from about 0.1 to 100% w/w of the formulation.

In a further embodiment, the present invention provides a pharmaceutical composition comprising, as active ingredient, a compound of the invention together, and/or in admixture, with at least one pharmaceutical carrier or diluent.

The carrier is pharmaceutically acceptable and must be compatible with, i.e. not have a deleterious effect upon, the other ingredients in the composition. The carrier may be a solid or liquid and is preferably formulated as a unit dose formulation, for example, a tablet which may contain from about 0.05 to 95% by weight of the active ingredient. If desired, other physiologically active ingredients may also be incorporated in the pharmaceutical compositions of the invention.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

In one embodiment, a pharmaceutical composition is administered in a dosage form which comprises a compound of the invention in a daily total amount of from about 0.1-1500 mg, 0.2-1200 mg, 0.3-1000 mg, 0.4-800 mg, 0.5-600 mg, 0.6-500 mg, 0.7-400 mg, 0.8-300 mg, 1-200 mg, 1-100 mg, 1-50 mg, 1-30 mg, 4-26 mg, 5-25 mg, or 5-10 mg.

A compound of the invention can be used in combination with other hepatocellular carcinoma treating drugs, such as anticancer chemotherapeutic drugs, hormones, biological response modifier(s), and other angiogenesis inhibitors; or in combination with immunotherapy or gene therapy.

EXAMPLE 1

Synthesis of Compound 1

Compound 1 can be prepared by methods known in the art (e.g., those described in U.S. Pat. No. 7,932,244). For example, Compound 1 can be prepared by a process as shown in Scheme 1 and disclosed in WO 2014/066819.

Scheme 1

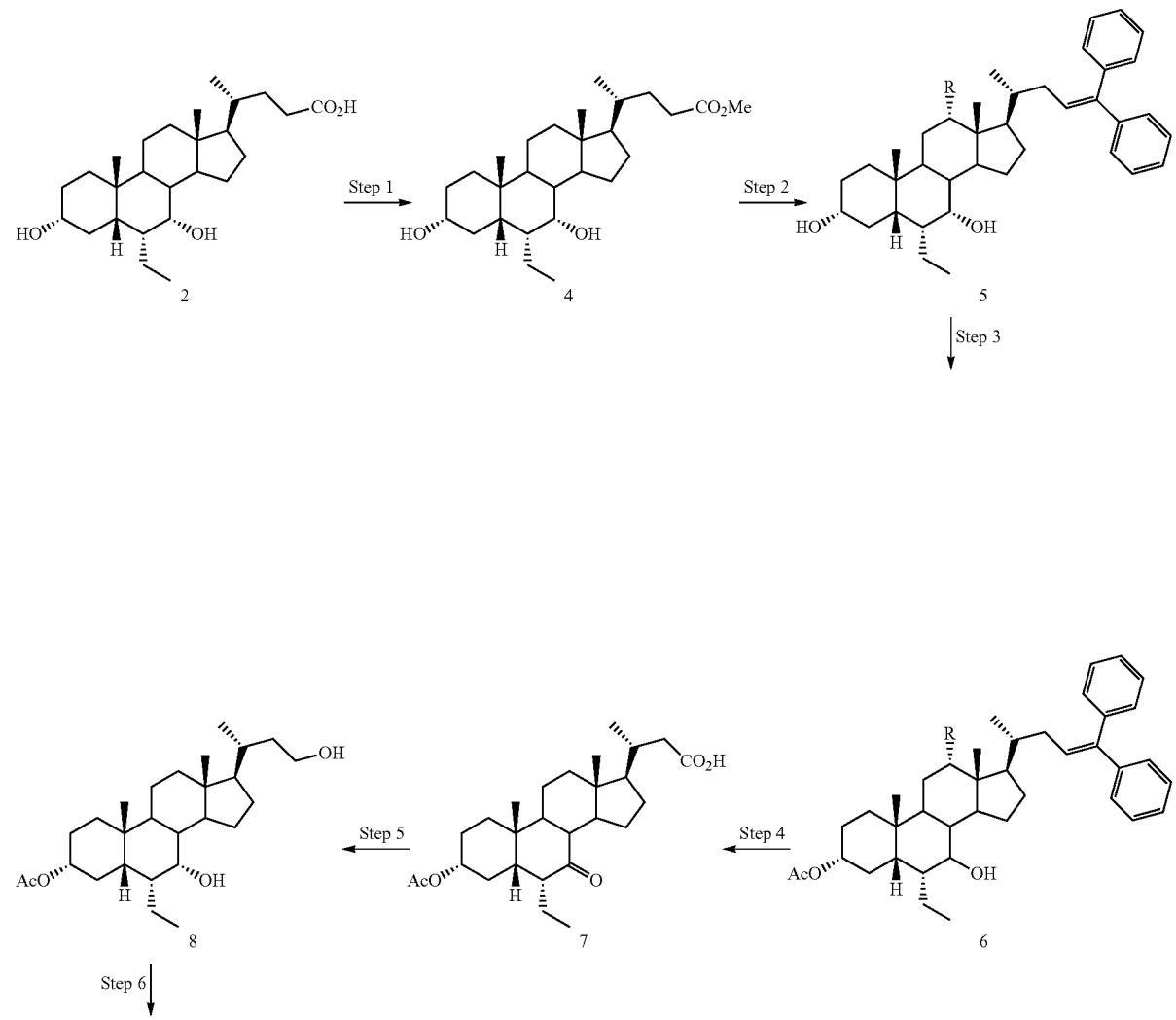

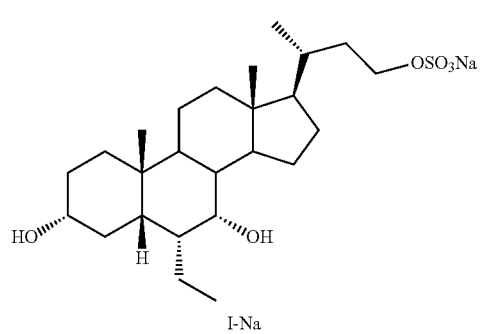

I-Na

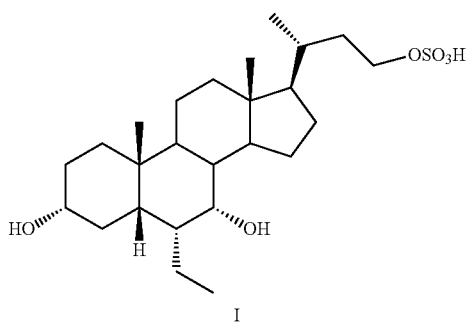

I

Step 1 is the esterification of Compound 2 to obtain Compound 4. Step 2 is a reaction to form Compound 5 from Compound 4. Step 3 is the protection of the hydroxyl group at the C3 position of Compound 5 to afford Compound 6. Step 4 is the oxidative cleavage of Compound 6 to afford Compound 7. Step 5 is the reduction of Compound 7 to afford Compound 8. Step 6 is the sulfonation of Compound 8 to afford the sodium salt of Compound 1 (1-Na). The sodium salt of Compound 1 can be converted to its free acid form (i.e., Compound 1) or other salt forms (e.g., Compound 1-DEA or the N,N-diethylethaneamine salt of Compound 1) according to procedures known in the art.

EXAMPLE 2

Synthesis of Compound 2

Compound 2 can be prepared by the conventional methods (e.g., those described in U.S. Publication No. 2009/0062526, U.S. Pat. No. 7,138,390, and WO 2006/122977), such as by a 6-step synthesis followed produce Compound 1 (obeticholic acid, or INT-747) as shown in Scheme 2 below.

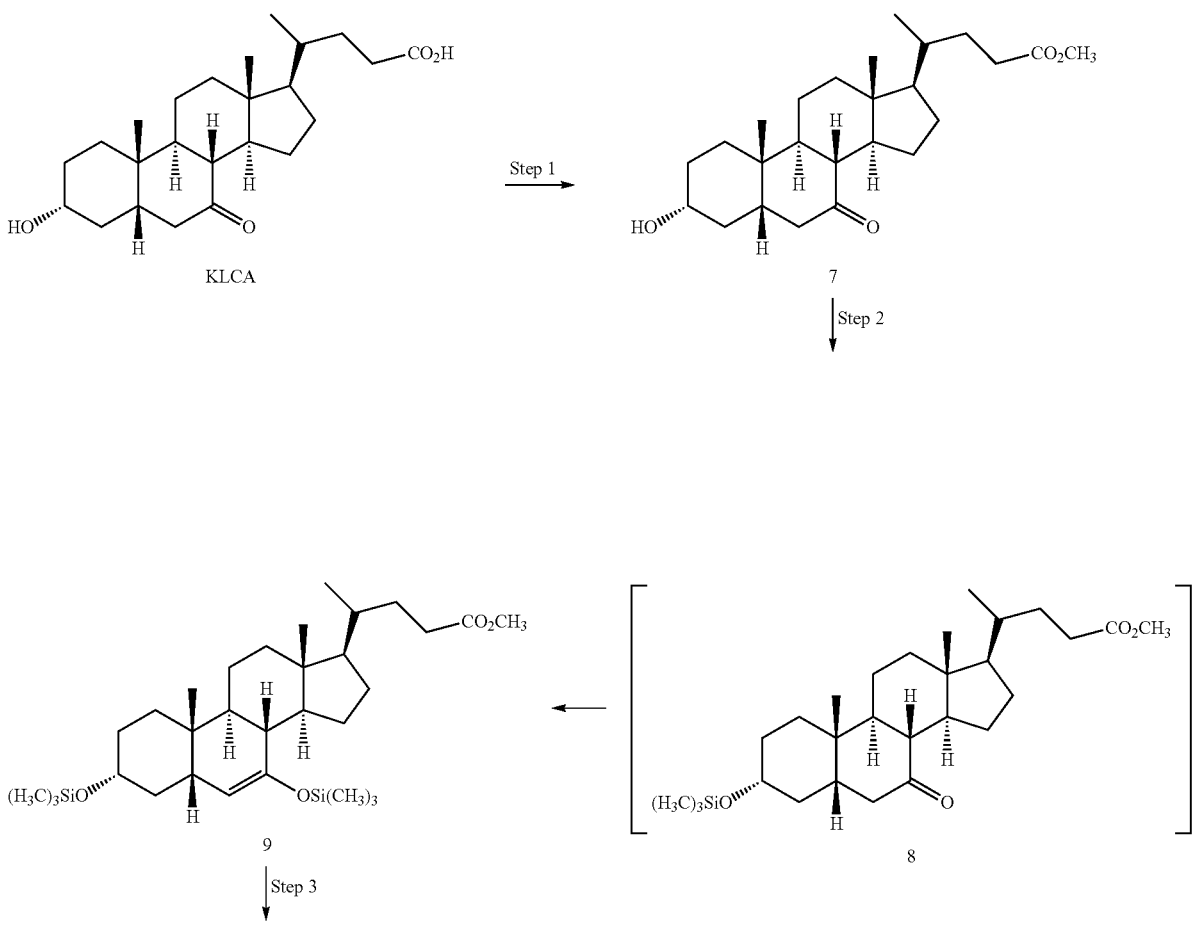

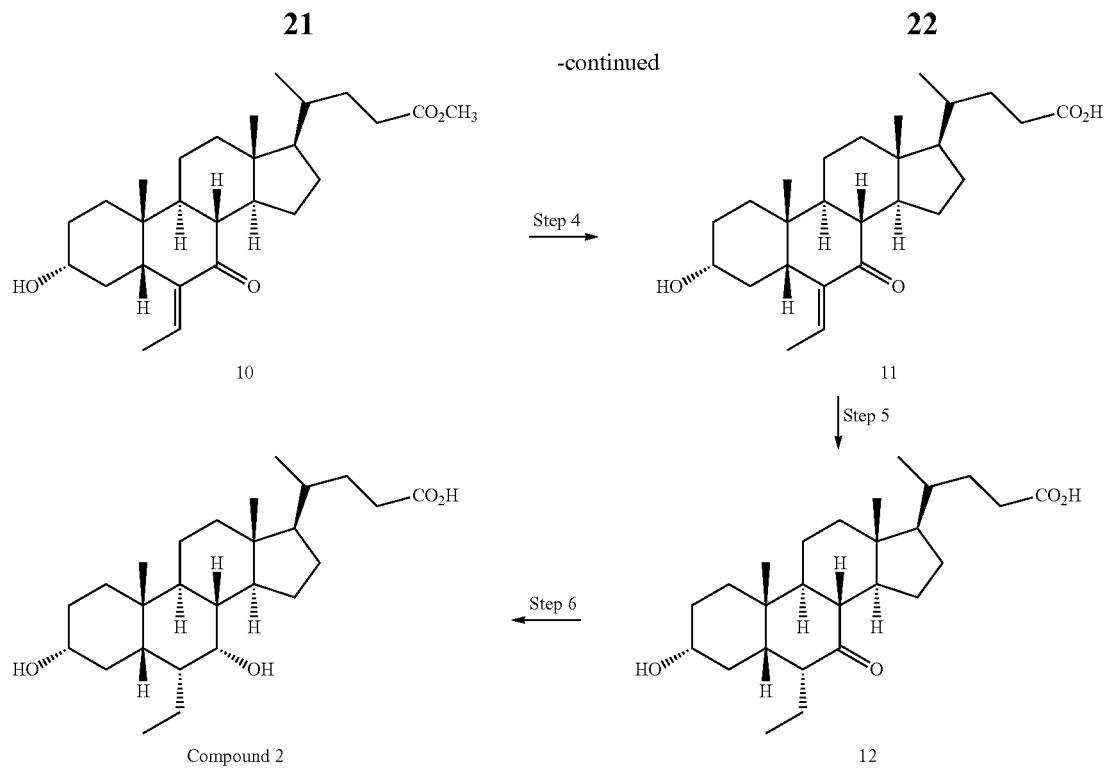

Compound 2

The process above is a 6-step synthesis. Step 1 is the esterification of the C-24 carboxylic acid of 7-keto lithocholic acid (KLCA) using methanol in the presence of acidic catalyst and heat to produce the methyl ester Compound 7. Step 2 is silylenol ether formation from Compound a using a strong base followed by treatment with chlorosilane to produce Compound 8. Step 3 is an aldol condensation reaction of the silylenol ether of compound 8 and acetaldehyde to produce Compound 10. Step 4 is saponification of the C-24 methyl ester of Compound 10 to produce Compound 11. Step 5 is the hydrogenation of the 6-ethylidene moiety of Compound 11 to produce compound 12. Step 6 is the selective reduction of the 7-keto group of Compound 12 to a 7α-hydroxy group to produce Compound 1.

EXAMPLE 3

Hepatocarcinogenesis in Mdr2$^{-/-}$ and FXR$^{-/-}$ Mice

The multidrug resistance protein 2 (Abcb4) is a member of the superfamily of ATP-binding cassette (ABC) transporters. The multidrug resistance protein 2 gene knockout mice (Mdr2$^{-/-}$) provides an in-vivo model of spontaneous hepatocarcinogenesis (Katzenellengoben, et al. Mol. Cancer Res. 2007, 5, 11, 1159-1170). Mice lacking the Abc4 protein encoded by the multidrug resistance-2 gene develop chronic periductular inflammation and cholestatic liver disease resulting in the development of hepatocellular carcinoma.

The farnesoid X receptor protein (FXR) is a nuclear receptor that functions as a bile acid sensor controlling bile acid homeostasis. This receptor is highly expressed in the liver and other organs. FXR knockout (FXR$^{-/-}$) mice develop hepatocellular adenoma and carcinoma after 15 months of age (Yang, et al. Cancer Res., 2007, 67, 863).

The effects of INT-747, INT-767, and control diet in Mdr2$^{-/-}$ and FXR$^{-/-}$ mice on the development of hepatocellular carcinoma were evaluated. INT-747 is a FXR agonist while INT-767 is a dual FXR/TGR5 agonist. The potency of INT-767 for FXR is about 10 fold greater than INT-747.

Study Design

Mdr2$^{-/-}$ and FXR$^{-/-}$ mice were randomly divided into three experimental groups.

The mice were fed a specific rodent diet or a diet supplemented with INT-747, INT-767, or control diet for 15 months. All mice were housed under pathogen-free conditions in a temperature-controlled room (23° C.) on a 12-hour light/dark cycle and drank water ad libitum. The Ethical Committee of the University of Bari approved this experimental set-up, which also was certified by the Italian Ministry of Health in accordance with internationally accepted guidelines for animal care. After 16 months, the mice were sacrificed and serum, liver and intestine were collected. The total number of hepatic tumors was counted and the diameter of each tumor was measured.

Treatment Groups

Group 1: Control Diet
    Mice (n=4) were fed control diet for 15 months.
Group 2: INT-747
    Mice (n=8) were fed control diet supplemented with OCA at a dose of 10 mg/kg for 15 months.
Group 3: INT-767
    Mice (n=15) were fed control diet supplemented with INT-767 at a dose of 10 mg/kg for 15 months.

Results

Liver inflammation and toxicity induced by bile salts in Mdr2$^{-/-}$ mice lead to the development of hepatocyte displasia. By 16 months of age, nearly 100% of the Mdr2$^{-/-}$ control mice developed liver tumors. FXR$^{-/-}$ mice aged 16 months developed spontaneous hepatocellular carcinoma.

Tumor Reduction and Size

Figure 1B:
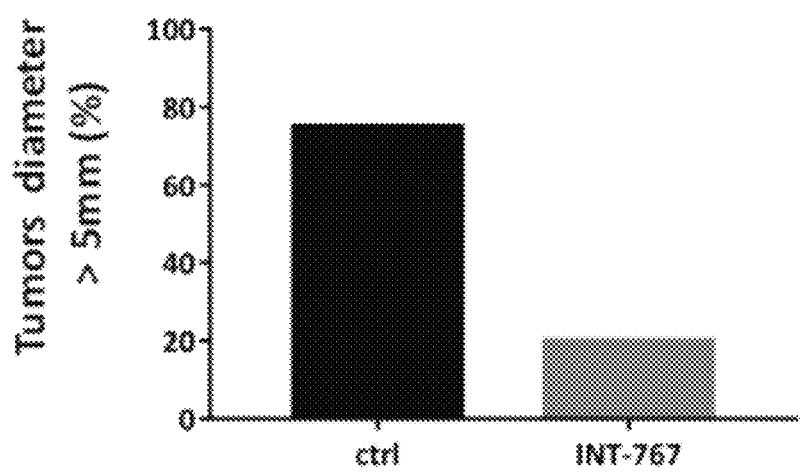
FIG. 1B is a bar graph showing the effects of INT-767 and control diet on the percent reduction of tumors (>5 mm diameter) in Mdr2$^{-/-}$ mice.
Figure 2A:
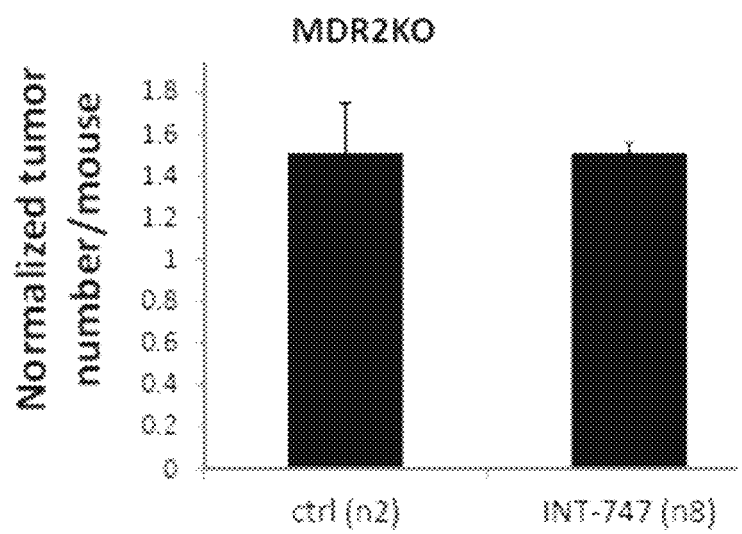
FIG. 2A is a bar graph showing the effects of INT-747 (Compound 2) and control diet on the number of hepatic tumors Mdr2$^{-/-}$ knockout mice.
Figure 2B:
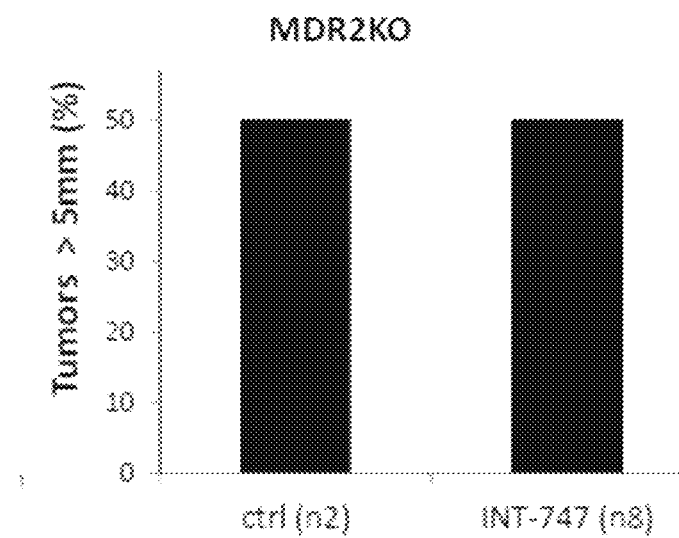
FIG. 2B is a bar graph showing the effects of INT-747 and control diet on the percent reduction of tumors (>5 mm diameter) in Mdr2$^{-/-}$ mice.
Figure 3A:
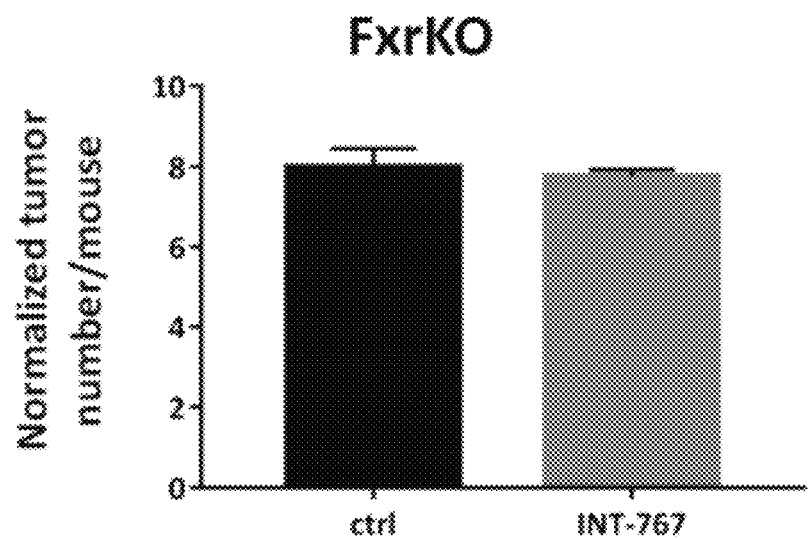
FIG. 3A is a bar graph showing the effects of INT-767 and control diet on the number of hepatic tumors in Farnesoid X Receptor (FXR$^{-/-}$) mice.
Figure 3B:
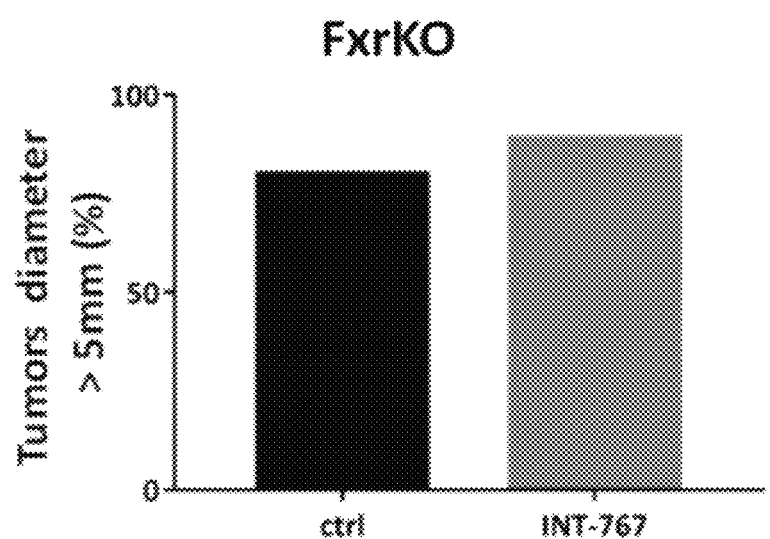
FIG. 3B is a bar graph showing the effects of INT-767 and control diet on the percent reduction of tumors (>5 mm diameter) in FXR$^{-/-}$ mice.
Figure 4:
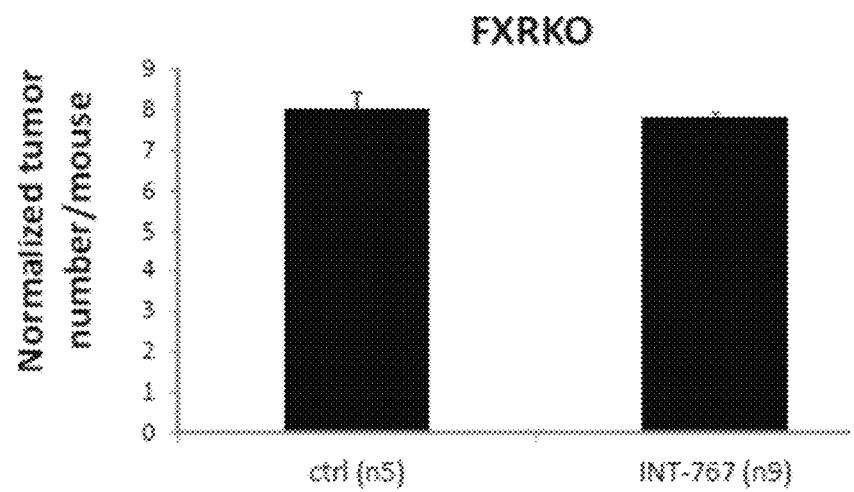
FIG. 4 is a bar graph showing the effects of INT-747 and control diet on the percent reduction on the number of hepatic tumors in FXR$^{-/-}$ mice.

FIGS. 1A and 2A show the effect of INT-767, INT-747, and control on the reduction of the number of tumors in Mdr2$^{-/-}$ mice. INT-767 clearly prevented hepatocellular carcinoma development in this study compared to control. Statistical significance was nearly observed (p=0.055) for the INT-767 group but not achieved due to the low number of control animals (n=2) used in the study. Mdr2$^{-/-}$ control mice and INT-747 treated mice displayed clearly identifiable liver tumors while minute tumors were found in INT-767 group. FIGS. 1B and 2B show the effects of INT-767, INT-747, and control on percent reduction of tumors having a diameter of >5 mm. Nearly 80% of the tumors found in the INT-747 and control groups had a diameter larger than 5 mm in Mdr2$^{-/-}$ mice. In contrast, FXR$^{-/-}$ mice treated with INT-767, INT-747, and control exhibited several large liver tumors indicating that the prevention of hepatocellular carcinoma development is mostly FXR dependent (FIGS. 3A, 3B and 4).

Liver Weight/Body Weight (LW/BW)

Figure 5A:
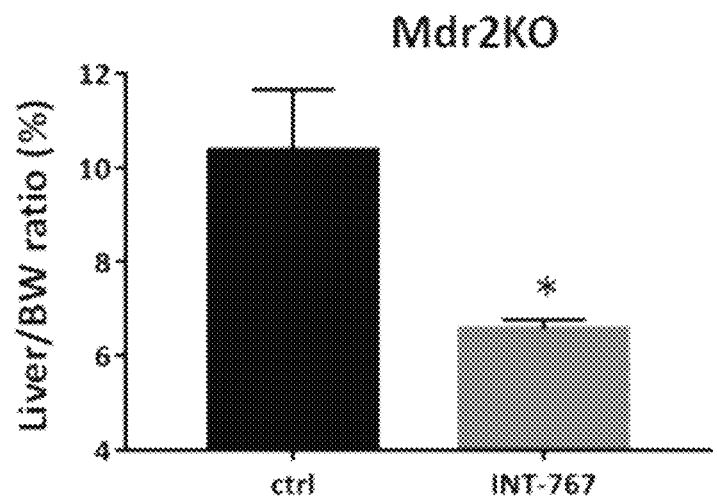
FIG. 5A is a bar graph showing the effects of INT-767 and control diet on the percent reduction on liver/body weight ratio in Mdr2$^{-/-}$ mice. *$p<0.01$ vs. control.
Figure 5B:
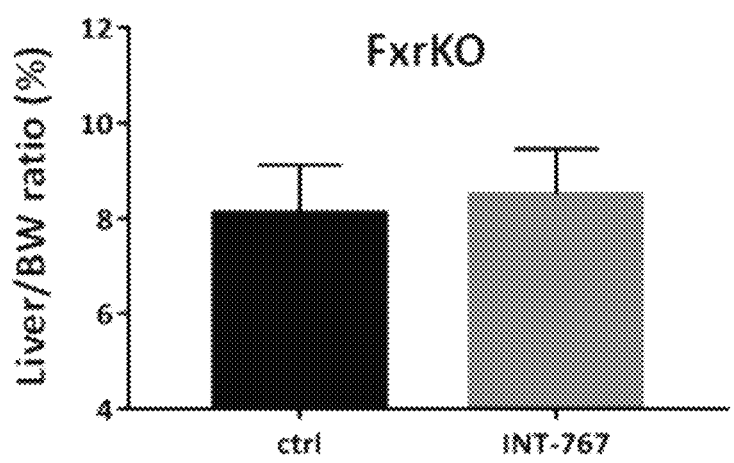
FIG. 5B is a bar graph showing the effects of INT-767 and control diet on the percent reduction on liver/body weight ratio in FXR$^{-/-}$ mice.

FIGS. 5A and 5B describe the effect of INT-767 and control on the percent ratio of liver and body weight. Consistent with previously generated data, the INT-767 treated Mdr2$^{-/-}$ mice exhibited a significant reduction in LW/BW ratio compared to control and INT-747 treated Mdr2$^{-/-}$ mice. No difference in LW/BW ratio was observed in the FXR$^{-/-}$ groups.

Biochemical Parameters

Figure 6A:
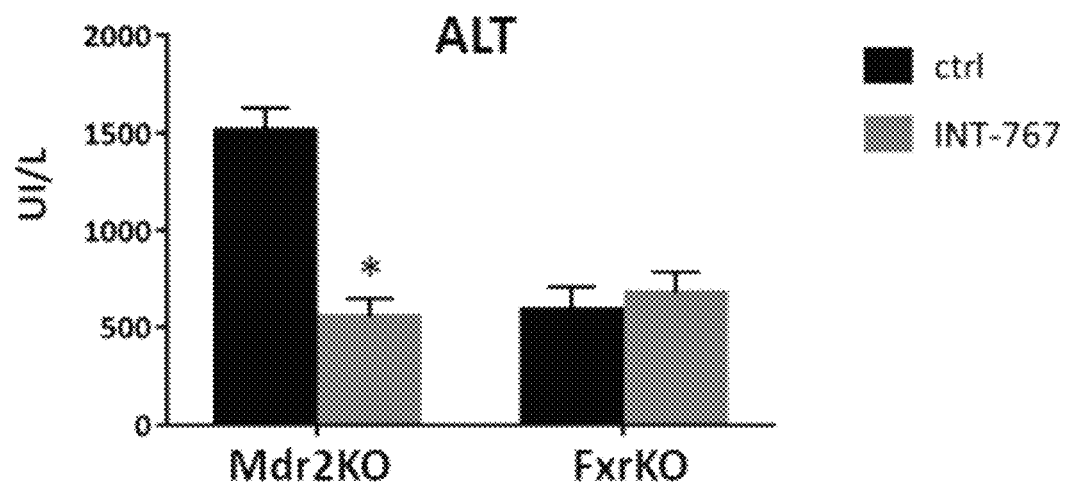
FIG. 6A is a bar graph showing the effect of INT-767 and control diet on alanine transaminase (ALT) levels in Mdr2$^{-/-}$ and FXR$^{-/-}$ mice. *$p<0.01$ vs. control.
Figure 6B:
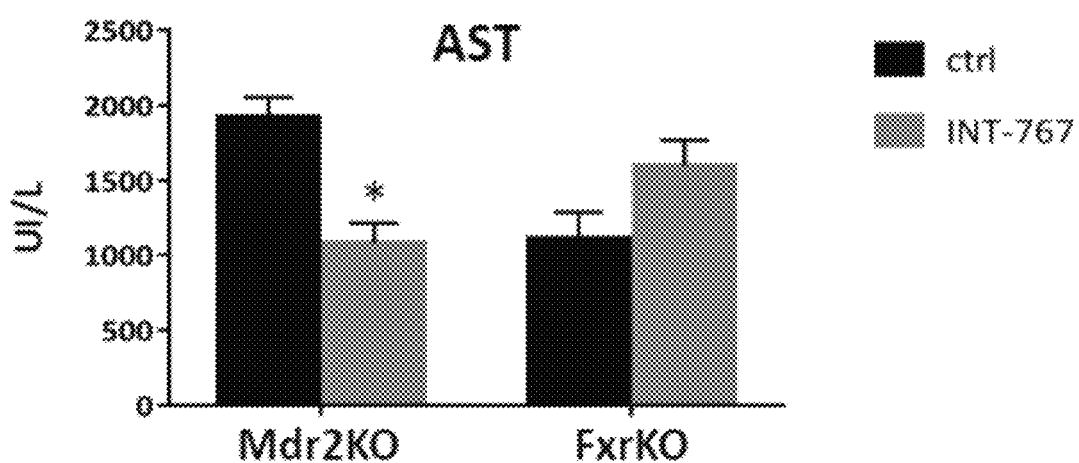
FIG. 6B is a bar graph showing the effect of INT-767 and control diet on aspartate transaminase (AST) levels in Mdr2$^{-/-}$ and FXR$^{-/-}$ mice. *$p<0.01$ vs. control.

In order to evaluate liver damage in Mdr2$^{-/-}$ and FXR$^{-/-}$ mice, the effect of INT-767 and control on the levels of liver enzymes, alanine aminotransferase (ALT) and aspartate aminotransferase (AST), was analyzed. As indicated in FIGS. 6A and 6B, treatment with INT-767 significantly reduced ALT and AST levels in Mdr2$^{-/-}$ mice. However, no difference in ALT and AST levels were observed in FXR$^{-/-}$ treated mice.

Ileal FXR Target Gene Expression

Figure 7A:
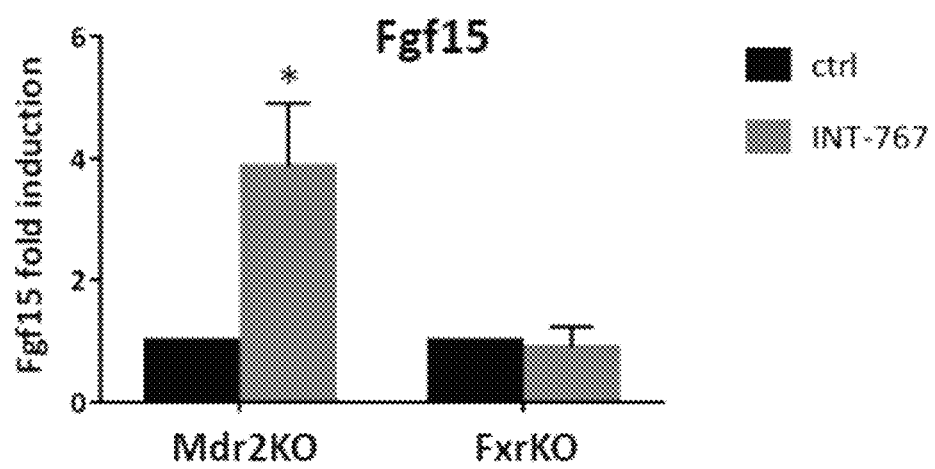
FIG. 7A is a bar graph showing the effect of INT-767 and control diet on ileal gene expression of fibroblast growth factor 15 (Fgf15) in Mdr2$^{-/-}$ and FXR$^{-/-}$ mice. *$p<0.01$ vs. control.
Figure 7B:
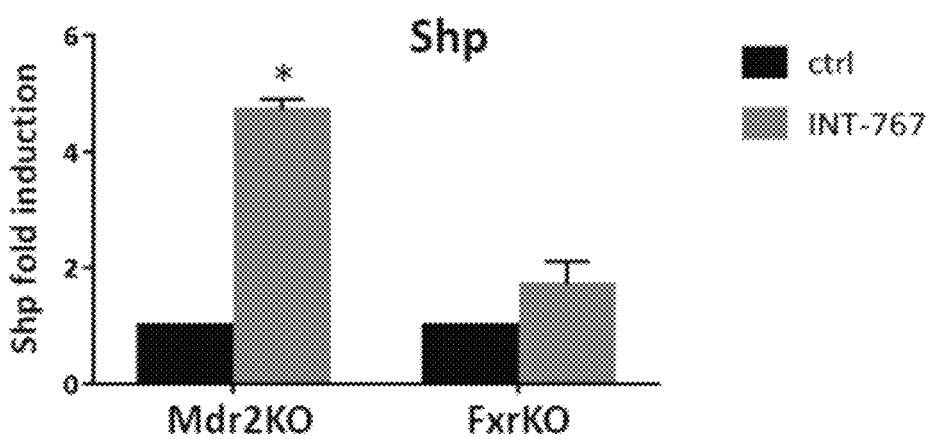
FIG. 7B is a bar graph showing the effect of INT-767 and control diet on ileal gene expression of small heterodimer partner (Shp) in Mdr2$^{-/-}$ and FXR$^{-/-}$ mice. *$p<0.01$ vs. control

To demonstrate the involvement of FXR in the prevention of hepatocellular carcinoma, the effect of of INT-767 and control on ileal FXR target gene expression was evaluated. As expected, both INT-747 and INT-767 stimulated fibroblast growth factor 15 (Fgf15) and small heterodimer partner (Shp) gene expression in Mdr2$^{-/-}$ groups only (FIGS. 7A and 7B).

Hepatic FXR Target Gene Expression

Figure 8:
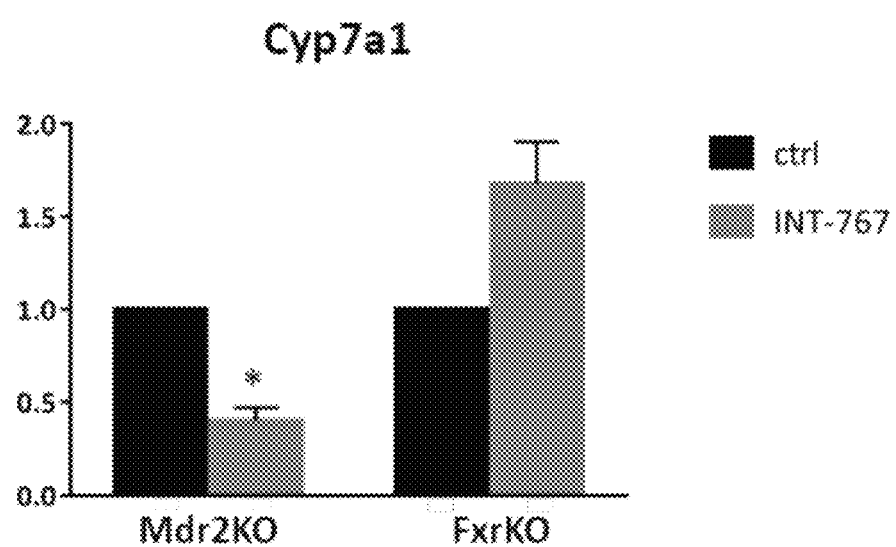
FIG. 8 is a bar graph showing the effect of INT-767 and control diet on the downregulation of cholesterol 7 alpha-hydroxylase (cyp7a1) in Mdr2$^{-/-}$ and FXR$^{-/-}$ mice. *$p<0.01$ vs. control
Figure 9A:
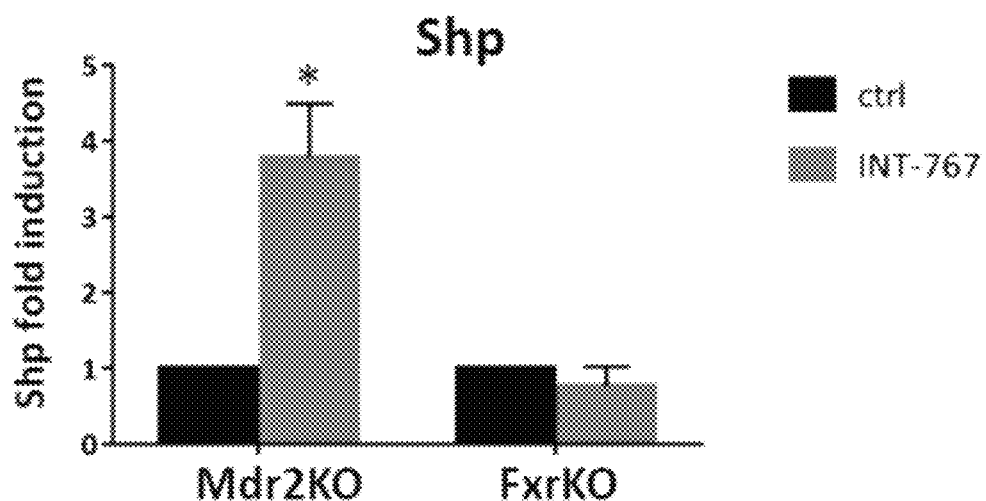
FIG. 9A is a bar graph showing the effect of INT-767 and control diet on hepatic gene expression of small heterodimer partner (Shp) in Mdr2$^{-/-}$ and FXR$^{-/-}$ mice. *$p<0.01$ vs. control.
Figure 9B:
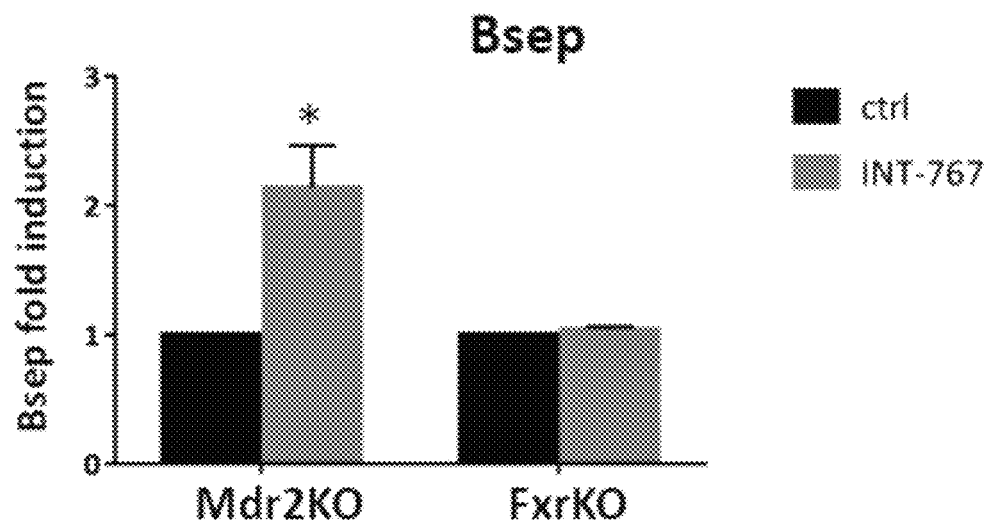
FIG. 9B is a bar graph showing the effect of INT-767 and control diet on hepatic gene expression of bile salt export pump (Bsep) in Mdr2$^{-/-}$ and FXR$^{-/-}$ mice. *$p<0.01$ vs. control

Cholesterol 7 alpha-hydroxylase (cyp7a1) is the rate limiting enzyme in the classical biosynthetic pathways which convert cholesterol into bile acids. Both INT-767 and INT-747 inhibited Cyp7a1 gene expression in Mdr2$^{-/-}$ mice only (FIG. 8). The bile salt export pump (Bsep) is a membrane protein that uses energy of ATP hydrolysis to actively transport bile acid salts. As indicated in FIGS. 9A and 9B, INT-767 administration induced hepatic Bsep activation in Mdr2$^{-/-}$ mice. INT-747 did not promote hepatic Bsep induction suggesting that in contrast to INT-767, which efficiently activates FXR in intestine and liver, INT-747 is less likely to have hepatic activity in Mdr2$^{-/-}$ mice.

Serum Total Bile Acids

Figure 10A:
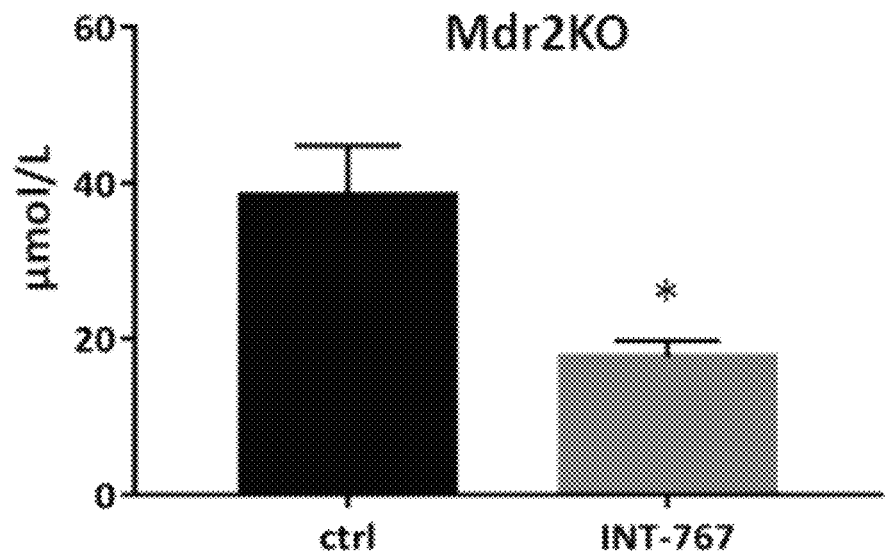
FIG. 10A is a bar graph showing the effect of INT-767 and control diet on the total serum bile acids in Mdr2$^{-/-}$ mice. *$p<0.01$ vs. control.
Figure 10B:
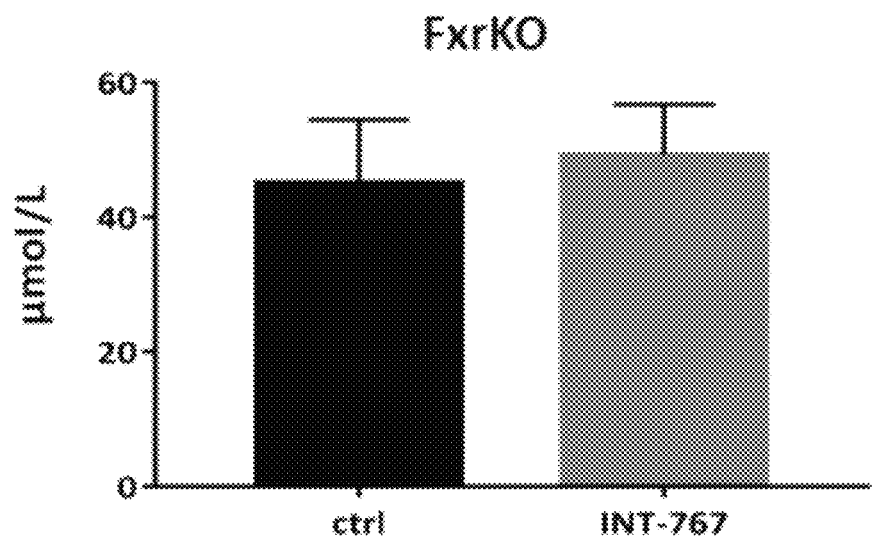
FIG. 10B is a bar graph showing the effect of INT-767 and control diet on the total serum bile acids in FXR$^{-/-}$ mice.

INT-767 significantly reduced serum bile acid levels in Mdr2$^{-/-}$ mice (FIG. 10A). The FXR dependence of this finding was confirmed by the observation that no reduction occurred in FXR$^{-/-}$ mice (FIG. 10B).

The invention claimed is:

1. A method of treating or preventing hepatocellular carcinoma in a subject in need thereof comprising administering a therapeutically effective amount of Compound 1:

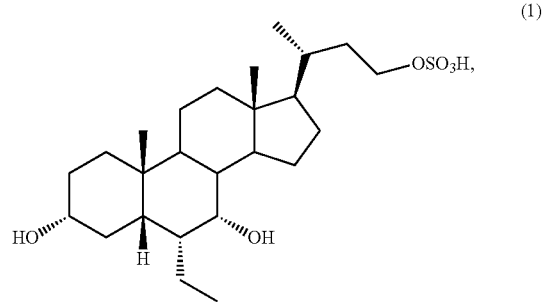

(1)

or a pharmaceutically acceptable salt thereof.

2. The method of claim 1, wherein the hepatocellular carcinoma is selected from the group consisting of early stage hepatocellular carcinoma, non-metastatic hepatocellular carcinoma, primary hepatocellular carcinoma, advanced hepatocellular carcinoma, locally advanced hepatocellular carcinoma, metastatic hepatocellular carcinoma, hepatocellular carcinoma in remission, or recurrent hepatocellular carcinoma.

3. The method of claim 1, wherein the FXR agonist is the sodium salt of Compound 1.

4. The method of claim 1, wherein the FXR agonist is the N,N-diethylethaneamine salt of Compound 1.

5. A method of treating or preventing hepatocellular carcinoma in a subject in need thereof comprising administering a pharmaceutical composition comprising a therapeutically effective amount of FXR agonist selected from Compound 1:

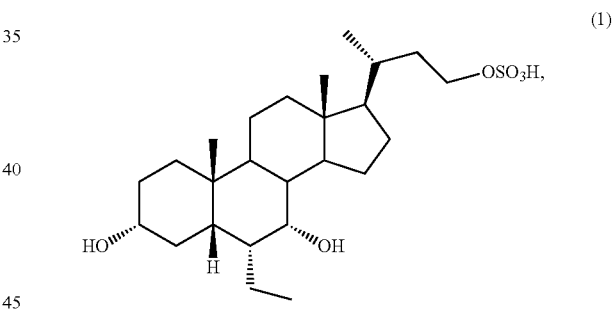

(1)

or a pharmaceutically acceptable salt thereof and a pharmaceutically acceptable excipient.

6. A kit for treating or preventing hepatocellular carcinoma in a subject in need thereof comprising Compound 1:

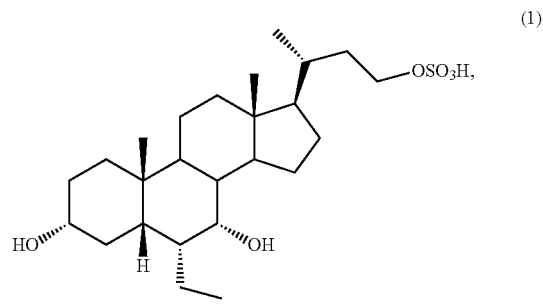

(1)

or a pharmaceutically acceptable salt thereof.

* * * * *